June 30, 1942. W. E. LAMMERTS Plant Pat. 528
PEACH TREE
Filed Sept. 19, 1941
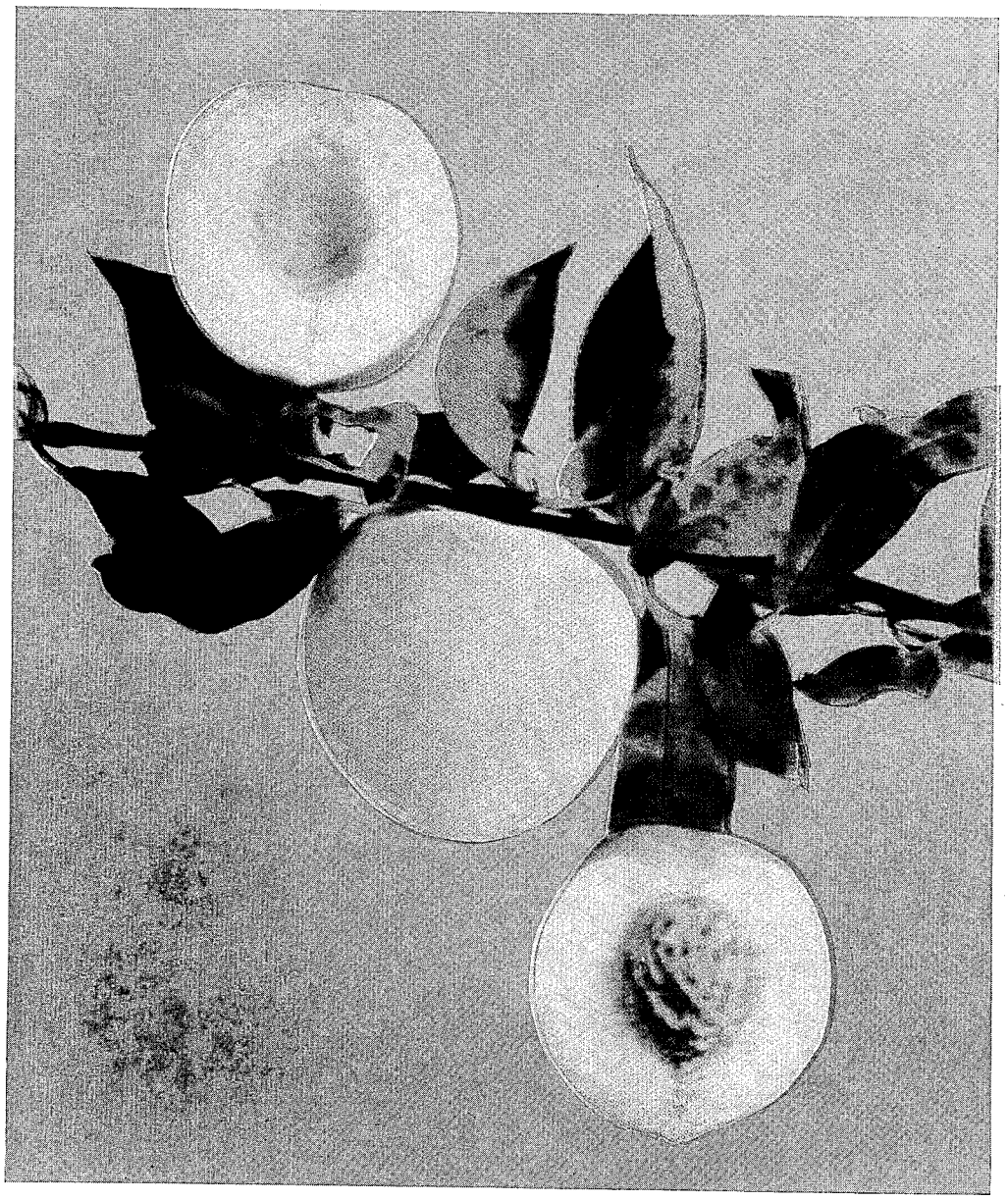
Inventor
W. E. Lammerts
By Robert Robb
Attorney Patented June 30, 1942

Plant Pat. 528

UNITED STATES PATENT OFFICE

528

PEACH TREE

Walter E. Lammerts, Ontario, Calif., assignor to Armstrong Nurseries, Inc., Ontario, Calif., a corporation of California Application September 19, 1941, Serial No. 411,575

1 Claim. (Cl. 47—62)

This invention relates to a new and distinct variety of peach tree, the result of carefully planned breeding, having as its objective the production of an early ripening peach suitable primarily for mild winter climates, such as prevail in the southern California section.

This new variety of peach represents a successful conclusion of the objective, and is primarily characterized as to novelty not only by the early ripening of the fruit, but also by the substantially uniform yellow flesh color thereof. The ripening date of this new peach is approximately twenty-eight days earlier than the well known peach variety "Early Imperial" grown under comparable conditions, it being understood that the observations regarding the same followed a winter during which three hundred hours of temperatures at 40° F., or below, were experienced between November 15 and the succeeding January 15. The ripening date, so far as I am aware, is unequalled by any other yellow peach variety grown under the conditions of southern California, for which it was especially bred as aforesaid.

The length of time between the flowering and ripening of the fruit is the same as that of the "Early Imperial" peach, and the difference in ripening dates between the new variety and "Early Imperial" is due to the early flowering date of this new variety, which is approximately one month earlier than the "Early Imperial."

The leafing of this new variety also occurs approximately one month earlier than the variety "Early Imperial," and because of these characteristics referred to the crop of fruit borne thereby is much more consistent in size, quality, and quantity than that of other varieties, such as the "Early Imperial."

Additionally, the new variety of peach herein referred to is characterized by a high skin color and by the vigor of growth of the tree which is exceptionally strong; and the almost complete absence of variation in color in the light yellow flesh color of the fruit even about the stone.

In size, this new peach is comparable to that of "Early Imperial," and would, therefore, be classified as medium.

The accompanying drawing illustrates the fruit, in whole and in section, and the foliage, as nearly as such reproduction can be illustrated.

The following is a detailed description of the new variety, all color terminology being in accord with Ridgway's Color Standard:

Seedling:

*Female.*—Early Imperial Peach × Early Double Red Flowering Peach (unnamed seedling).

*Male.*—Socala Peach.

Tree: Large; vigorous; upright; spreading; open; vase-formed; very productive; regular bearer.

*Trunk.*—Medium stocky; medium smooth.

*Branches.*—Medium stocky; medium smooth; between Natal Brown, Plate XL, and Olive Brown, Plate XL; dull. *Lenticels.*—numerous; small.

*Leaves.*—Length—4–5 inches; width—1⅛ to 1½ inches. Large to medium; lanceolate; acutely pointed; medium to thin; upper side of mature leaves slightly lighter than Cress Green, Plate XXXI; under side of mature leaf slightly lighter than light Elm Green, Plate XVII; upper side of young leaf near Cosse Green, Plate V; under side of young leaf near Lettuce Green, Plate V; smooth. *Margin*—glandular; finely serrate. *Petiole*—medium to short; medium to slender. *Glands*—average number—two, sometimes one, sometimes wanting. Opposite; small; globose; near Calliste Green, Plate VI. Position—on margin of leaflet just above petiole. *Stipules*—very narrow, being slightly wider at base than apex; early deciduous; irregular long teeth on margins.

*Flower Buds.*—Large; long; conic; pointed.

*Flowers.*—Dates first and full bloom—around February 22 and 26, respectively, for southern California. Early compared with other varieties. Large to medium. Reddish in color.

Fruit: Maturity when described—eating ripe about June 15.

*Size.*—Uniform; medium large. Diameter axial—2–2⅛ inches. Transverse in suture plane—2⅛ to 2¼ inches. At right angles to suture plane—1⅞ to 2 inches.

*Form.*—Uniform; unsymmetrical; broadly ovoid; compressed laterally toward suture on one side.

*Suture.*—Distinct; fairly shallow; extends from base to beyond apex; has slight depression beyond pistil point.

*Ventral surface.*—Strongly lipped toward apex on left side. *Lips*—unequal.

*Cavity.* — Rounded. Depth — ⅗ inch. Breadth—⅘ inch. Markings—none.

*Base.*—Oblique.

*Apex.*—Short; rounded. *Pistil point*—very inconspicuous.

*Stem.*—Length—$\frac{3}{16}$ inch. Medium slender; glabrous. *Adherence to stone*—strong.

*Skin.*—Thin; medium to tender; free. Tendency to crack—none. *Color*—basic color between and varying from Capucine Yellow, Plate III, and Light Orange Yellow, Plate III, blushed or overlaid where exposed to the sun with Peach Red, Plate I, and so thickly dotted over the entire surface (except immediately around the stem) with small dots near Carmine, Plate I, as to give the appearance of solidity of coloring. *Down*—moderate; medium long; rolls up when rubbed.

Flesh:

*Color.*—Near Pale Orange Yellow, Plate III, with near Eosine Pink, Plate I, flecks near apex and somewhat more lightly at base.

*Surface of pit cavity.*—Near Apricot Yellow, Plate IV, with fibers same color.

*Amygdalin.*—Moderate to scant, juice—abundant; fairly rich.

*Texture.*—Medium firm; fine; melting.

*Fibres.*—Uneven; earliest at apex along larger lip.

*Ripens.*—Earliest along larger lips.

*Flavor.*—Subacid; mild.

*Aroma.*—Pronounced.

*Eating quality.*—Good.

Stone: Free. Adheres to flesh along both dorsal and ventral edges over upper half of sides. Retains short fiber like threads along ridges.

*Size.*—Medium to small.

*Length.*—$1\frac{3}{16}$ inches.

*Breadth.*—$\frac{4}{5}$ inch.

*Thickness.*—$\frac{3}{5}$ inch.

*Form.*—Ovoid; full toward base.

*Base.*—Straight. *Apex*—acuminate.

*Sides.*—About equal; curved on right and left sides. *Surface*—irregularly furrowed toward apex; ridged near base; pitted throughout.

*Ridges.*—Jagged toward apex.

*Pits.*—Circular. *Ventral edges*—thick with wing toward base.

*Dorsal edge.*—Narrow with shallow narrow groove to above center. Ridges on either side—interrupted.

*Color of stone.*—Near Pinkish Cinnamon, Plate XXIX, with strong markings of Eosine Pink, Plate I, along ventral edge, about stem and apex.

*Tendency to split.*—Slight.

Use: Market; local.

Keeping quality: Good to medium.

Resistance to:

*Insects.*—Medium.

*Diseases.*—Medium.

Shipping quality: Medium.

I claim:

A new and distinct variety of peach tree characterized as to novelty by its early ripening period, its vigorous growth and exceptional strength; the early flowering and leafing resulting in consistency in size, quality, and quantity of its fruit as compared with other early varieties; the yellow flesh coloring of the fruit, and almost complete absence of variation in this light yellow flesh color, substantially as shown and described.

WALTER E. LAMMERTS.